(12) United States Patent
Vath

(10) Patent No.: US 8,815,309 B2
(45) Date of Patent: Aug. 26, 2014

(54) METHODS OF TREATING A SUBJECT WITH BENIGN PROSTATE HYPERPLASIA

(75) Inventor: James E. Vath, Lynnfield, MA (US)

(73) Assignee: Zafgen, Inc., Cambridge, MA (US)

( * ) Notice: Subject to any disclaimer, the term of this patent is extended or adjusted under 35 U.S.C. 154(b) by 0 days.

(21) Appl. No.: 13/520,744

(22) PCT Filed: Jan. 7, 2011

(86) PCT No.: PCT/US2011/020515
§ 371 (c)(1),
(2), (4) Date: Nov. 13, 2012

(87) PCT Pub. No.: WO2011/085198
PCT Pub. Date: Jul. 14, 2011

(65) Prior Publication Data
US 2013/0052283 A1   Feb. 28, 2013

Related U.S. Application Data

(60) Provisional application No. 61/293,320, filed on Jan. 8, 2010.

(51) Int. Cl.
*A61K 36/00* (2006.01)
*A61K 36/889* (2006.01)

(52) U.S. Cl.
USPC .......................................... 424/727; 424/725

(58) Field of Classification Search
None
See application file for complete search history.

(56) References Cited

U.S. PATENT DOCUMENTS

| | | | |
|---|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,242,494 B1 | 6/2001 | Craig et al. |
| 6,277,391 B1 | 8/2001 | Seo et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,887,863 B2 | 5/2005 | Craig et al. |
| 6,989,392 B2 | 1/2006 | Collins et al. |
| 7,030,262 B2 | 4/2006 | BaMaung et al. |
| 7,037,890 B2 | 5/2006 | Olson et al. |
| 7,084,108 B2 | 8/2006 | Olson et al. |
| 7,268,111 B2 | 9/2007 | Olson et al. |
| 7,304,082 B2 | 12/2007 | Marino, Jr. et al. |
| 7,718,695 B2 | 5/2010 | Kim et al. |
| 8,367,721 B2 | 2/2013 | Hughes et al. |
| 2002/0002152 A1 | 1/2002 | Craig et al. |
| 2003/0220371 A1 | 11/2003 | Kallander et al. |
| 2004/0067266 A1 | 4/2004 | Toppo |
| 2004/0116495 A1 | 6/2004 | Marino Jr. et al. |
| 2004/0157836 A1 | 8/2004 | Comess et al. |
| 2004/0167128 A1 | 8/2004 | Comess et al. |
| 2004/0192914 A1 | 9/2004 | Kallander et al. |
| 2004/0204472 A1 | 10/2004 | Briggs et al. |
| 2005/0004116 A1 | 1/2005 | Kallander et al. |
| 2005/0037994 A1 | 2/2005 | Kim et al. |
| 2005/0113420 A1 | 5/2005 | Nan et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |

FOREIGN PATENT DOCUMENTS

| | | |
|---|---|---|
| EP | 0682020 A1 | 11/1995 |
| WO | WO-98/56372 A1 | 12/1998 |

(Continued)

OTHER PUBLICATIONS

Anderson "The Use of Fumagillin in Amoebiasis", Ann N Y Acad Sci. Dec. 30, 1952;55(6):1118-24.
Benny, et al., "An Orally Delivered Small-Molecule Formulation with Antiangiogenic and Anticancer Activity", Nat Biotechnol. Jul. 2008;26(7):799-807. doi: 10.1038/nbt1415. Epub Jun. 29, 2008.
Didier, et al. "Antimicrosporidial Activities of Fumagillin, TNP-470, Ovalicin, and Ovalicin Derivatives in Vitro and In Vivo", Antimicrob Agents Chemother. Jun. 2006;50(6):2146-55.

(Continued)

*Primary Examiner* — Qiuwen Mi
(74) *Attorney, Agent, or Firm* — Goodwin Procter LLP

(57) ABSTRACT

The invention generally relates to methods of treating a male subject with a prostate condition, for example, benign prostate hyperplasia (BPH). In certain embodiments, the invention provides methods of treating a male subject with a prostate condition, which include administering a MetAP2 inhibitor at a dose that does not substantially modulate angiogenesis.

20 Claims, No Drawings

(56) References Cited

FOREIGN PATENT DOCUMENTS

| WO | WO-99/39702 A2 | 8/1999 |
|---|---|---|
| WO | WO-99/57097 A2 | 11/1999 |
| WO | WO-99/59986 A1 | 11/1999 |
| WO | WO-99/59987 | 11/1999 |
| WO | WO-00/64876 A1 | 11/2000 |
| WO | WO-02/26782 A2 | 4/2002 |
| WO | WO-02/42295 A2 | 5/2002 |
| WO | WO-02/083065 A2 | 10/2002 |
| WO | WO-03/027104 A1 | 4/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 | 4/2013 |
| WO | WO-2013/109735 | 7/2013 |
| WO | WO-2013/109739 | 7/2013 |
| WO | WO-2013/169727 | 11/2013 |
| WO | WO-2013/169857 | 11/2013 |
| WO | WO-2013/169860 | 11/2013 |

OTHER PUBLICATIONS

Drevs, et al. "Antiangiogenic Potency of FK866/K22.175, a New Inhibitor of Intracellular NAD Biosynthesis, In Murine Renal Cell Carcinoma", Anticancer Res. Nov.-Dec. 2003;23(60):4853-8.
Dumas, et al., "Synthesis and Structure Activity Relationships of Novel Small Molecule Cathepsin D Inhibitors", Bioorg Med Chem Lett. Sep. 6, 1999;9(17):2531-6.
Eder, et al., "Phase 1 Dose Escalation Safety & Tolerance Study of PPI-2458 in Subjects with Non-Hodgkin's Lymphoma or Solid Tumors", (Presented on Nov. 7-10, 2006 at EORTC-NCI-AACR Symposium on "Molecular Targets and Cancer Therapeutics.").
European Search Report for EP 09798793 dated Oct. 11, 2011, 9 pages.
Evdokimov, et al. "Serendipitous discovery of novel bacterial methionine aminopeptidase inhibitors", Proteins. Feb. 15, 2007;66(3):538-46.
Everhart "Contributions of Obesity and Weight Loss to Gallstone Disease", Ann Intern Med. Nov. 15, 1993;119(10):1029-35.
Garrabrant ,et al. "Small molecule inhibitors of methionine aminopeptidase type 2 (MetAP-2) fail to inhibit endothelial cell proliferation or formation of microvessels from rat aortic rings in vitro", Angiogenesis. 2004;7(2):91-6.
Han, et al. "Design and Synthesis of Highly Potent Fumagillin Analogues from Homology Modeling for a Human MetAP-2", Bioorg Med Chem Lett. Jan. 3, 2000;10(1):39-43.
Huang, et al "Inhibition of monometalated methionine aminopeptidase: inhibitor discovery and crystallographic analysis", J Med Chem. Nov. 15, 2007;50(23):5735-42. Epub Oct. 19, 2007.
Ingber, et al. "Synthetic analogues of fumagillin that inhibit angiogenesis and suppress tumour growth", Nature. Dec. 6, 1990;348(6301):555-7.
International Search Report for International Application No. PCT/US2011/38352, International Filing Date May 27, 2011 (3 pages).
International Search Report for International Application No. PCT/US2011/020515, International Filing Date Jul. 1, 2011 (4 pages).
Jeong, et al, (2005) "Total Synthesis and Antiangiogenic Activity of Cyclopentane Analogues of Fumagillol", Bioorg Med Chem Lett. Aug. 1, 2005;15(15):3580-3.
Kawai, et al. "Development of sulfonamide compounds as potent methionine aminopeptidase type II inhibitors with antiproliferative properties", Bioorg Med Chem Lett. Jul. 1, 2006;16(13):3574-7. Epub May 2, 2006.
Kim, et al. "Development of parenteral formulation for a novel angiogenesis inhibitor, CKD-732 through complexation with hydroxypropyl-beta-cyclodextrin", Int J Pharm. Mar. 19, 2004;272(12):79-89.
Kim, et al. "Depletion of methionine aminopeptidase 2 does not alter cell response to fumagillin or bengamides", Cancer Res. May 1, 2004;64(9):2984-7.
Kim, et al. General pharmacology of CKD-732, a new anticancer agent: effects on central nervous, cardiovascular, and respiratory system, Biol Pharm Bull. Feb. 2005;28(2):217-23.
Kim, et al. "Assessment of the Anti-Obesity Effects of the TNP-470 Analog, CKD-732", J Mol Endocrinol. Apr. 2007;38(4):455-65.
Kruger, Erwin, A., "TNP-470: An Angiogenesis Inhibitor in Clinical Development for Cancer", Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs", Arch Pharm Res. Feb. 2004;27(2):265-72.
Lee et al. "Selective N-demethylation of tertiary aminofumagillols with selenium dioxide via a non-classical Polonovski type reaction", Heterocycles 68(5):915-932 2006.
Lee et al. "Design, Synthesis, and Antiangiogenic Effects of a Series of Potent Novel Fumagillin Analogues", Chem Pharm Bull (Tokyo). Jul. 2007;55(7):1024-9.
Lijnen, H.R., et al. "Fumagillin Reduces Adipose Tissue Formation in Murine Models of Nutritionally Induced Obesity", Obesity (Silver Spring). Dec. 2010;18(12):2241-6. doi: 10.1038/oby.2009.503. Epub Jan. 21, 2010.
Luo et al "Discovery and Structural Modification of Inhibitors of Methionine Aminopeptidases from *Escherichia coli* and Saccharomyces cerevisiae", J Med Chem. Jun. 19, 2003;46(13):2631-40.
Ma et al. "Structural analysis of inhibition of *E. coli* methionine aminopeptidase: implication of loop adaptability in selective inhibition of bacterial enzymes", BMC Struct Biol. Dec. 19, 2007;7:84.
Masiero, Laura, et al. "New Anti-angiogenesis Agents: Review of the Clinical Experience with Carboxyamido-Triazole (CAI), Thalidomide, TNP-470 and Interleukin-12", Angiogenesis. 1997;1(1):23-35.
McCowan, Max C., et al., "Fumagillin (H-3), a New Antibiotic with Amebicidal Properties", Science. Feb. 23, 1951;113(2930):202-3.
Milkowski, Deborah M., et al., Antiangiogenic Agents in Cancer Therapy, Chapter 22 "TNP-470," pp. 385-398, 2012.
Molina et al. "Potential Efficacy of Fumagillin in Intestinal Microsporidiosis Due to Enterocytozoon Bieneusi in Patients with HIV Infection: Results of a Drug Screening Study", AIDS. Nov. 1997;11(13):1603-10.
Molina et al. "Fumagillin Treatment of Intestinal Microsporidiosis", N Engl J Med. Jun. 20, 2002;346(25):1963-9.
Molina, et al. "Trial of Oral Fumagillin for the Treatment of Intestinal Microsporidiosis in Patients with HIV Infection", AIDS. Jul. 7, 2000;14(10):1341-8.
Myung et al. "The identification of in vitro metabolites of CKD-732 by liquid chromatography/tandem mass spectrometry", Rapid Commun Mass Spectrom. 2002;16(21):2048-53.

(56) References Cited

OTHER PUBLICATIONS

Naganuma, Yasuko, et al. "Metronomic Doxifluridine Chemotherapy Combined with the Anti-Angiogenic Agent TNP=470 Inhibits the Growth of Human Uterine Carcinosarcoma Xenografts", Cancer Sci. Aug. 2011;102(8):1545-52.
National Task Force on the Prevention and Treatment of Obesity (1993) "Very Low-Calorie Diets", JAMA 270(8):967-974.
Noel et al. "Increased Risk of Acute Pancreatitis and Biliary Disease Observed in Patients with Type 2 Diabetes", Diabetes Care. May 2009;32(5):834-8. doi: 10.2337/dc08-1755. Epub Feb. 10, 2009.
Pagliarulo et al. "Gallstone disease and related risk factors in a large cohort of diabetic patients", Dig Liver Dis. Feb. 2004;36(2):130-4.
Picoul et al. "Progress in fumagillin synthesis", Pure Appl. Chem., 2003, vol. 75, No. 2-3, pp. 235-249.
Rhee et al. "Angiogenesis inhibitor attenuates parathyroid hormone-induced anabolic effect", Biomed Pharmacother. Jan. 2009;63(1):63-8.
Rupnick, MA "Adipose Tissue Mass Can be Regulated Through the Vasculature", Proc Natl Acad Sci U S A. Aug. 6, 2002;99(16):10730-5.
Search Report completed on Mar. 2, 2011, for International Application PCT/US2010/052050.
Seneca et al. "Amebiasis: a review. II. Laboratory diagnosis, differential diagnosis and therapy," Am J Dig Dis. Jul. 1956;1(7):310-22.
Sheppard et al. "3-Amino-2-hydroxyamides and related compounds as inhibitors of methionine aminopeptidase-2", Bioorg Med Chem Lett. Feb. 23, 2004;14(4):865-8.
Shin et al. "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy", Invest New Drugs. Apr. 2012;30(2):672-80.
Shin, "A Phase I Pharmacokinetic and Pharmacodynamic Stdy of CKD-732, an Antiangiogenic Agent, in Patients with Refractory Solid Cancer", Invest New Drugs 28:650-658, (2010) Published online Dec. 29, 2010.
Srikumar et al. "Structural insights on Brugia malayi transglutaminase with cinnamoyl derivatives—a molecular docking approach", International Journal of Pharma and Bio Sciences 3(3):998-1006, 2012.
Teicher, et al "Antiangiogenic Agents in Cancer Therapy" pp. 385-398, 1999.
Towbin et al. "Proteomics-based target identification: bengamides as a new class of methionine aminopeptidase inhibitors", J Biol Chem. Dec. 26, 2003;278(52):52964-71.
Vedantham et al. "Studies towards the synthesis of methionine aminopeptidase inhibitors: diversification utilizing a ROMP-derived coupling reagent", J Comb Chem. Mar.-Apr. 2008;10(2):195-203.
Wang et al. "Discovery of inhibitors of *Escherichia coli* methionine aminopeptidase with the Fe(II)-form selectivity and antibacterial activity", J Med Chem. Oct. 9, 2008;51(19):6110-20.
Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.
Wang et al. "Tumor Suppression by a Rationally Designed Reversible Inhibitor of Methionine Aminopeptidase-2", Cancer Res. 63:7861-7869, 2003.
Weinsier et al. "Gallstone Formation and Weight Loss", Obes Res. Jan. 1993;1(1):51-6.
Weinsier, et al. "Medically Safe Rate of Weight Loss for the Treatment of Obesity: A Guideline Based on Risk of Gallstone Formation", Am J Med. Feb. 1995;98(2):115-7.
Winter et al. "Endothelial αvβ3 Integrin-Targeted Fumagillin Nanoparticles Inhibit Angiogenesis in Atherosclerosis", Arterioscler Thromb Vasc Biol. Sep. 2006;26(9):2103-9.
Written Opinion for International Application No. PCT/US2009/066816, mailed Apr. 8, 2010, 3 pages.
Yanai, Shigeo, et al. "Antitumor Effect of Arterial Administration of a Medium-Chain Triglyceride Solution of an Angiogenesis Inhibitor, TNP-470, in Rabbits Bearing VX-2 Carcinoma", Pharm Res. May 1995;12(5):653-7.
Yanai, Shigeo, et al., "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver", J Pharmacol Exp Ther. Dec. 1994;271 (3):1 267-73.
Zhang et al. "Angiogenesis inhibitors specific for methionine aminopeptidase 2 as drugs for malaria and leishmaniasis", J Biomed Sci. Jan.-Feb. 2002;9 1):34-40.
Anderson "The Use of Fumagillin in Amoebiasis", Ann N Y Acad Sci. Dec. 30, 1952; 55(6):1118-24.
Benny, et al., "An Orally Delivered Small-Molecule Formulation with Antiangiogenic and Anticancer Activity", Nat Biotechnol. Jul. 2008; 26(7):799-807. doi: 10.1038/nbt1415. Epub Jun. 29, 2008.
Bernier, et al. "Fumagillin class inhibitors of methionine aminopeptidase-2", Drugs of the Future 30(5): 497-500.
Brakenhielm, et al., "Angiogenesis Inhibitor, TNP-470, Prevents Diet-Induced and Genetic Obesity in Mice", Circulation Research, http://circres.ahajournals.org (accessed on Feb. 8, 2007).
Braunwald, et al, "Obesity" in Harrison's Principles of Internal Medicine, 15th Ed., McGraw Hill (New York) pp. 479-486.
Chun, et al. "Novel inhibitors targeted to methionine aminopeptidase 2 (MetAP2) strongly inhibit the growth of cancers in xenografted nude model", Int. J. Cancer 114(1):124-30.
Didier, et al. "Antimicrosporidial Activities of Fumagillin, TNP-470, Ovalicin, and Ovalicin Derivatives in Vitro and In Vivo", Antimicrob Agents Chemother. Jun. 2006; 50(6):2146-55.
DiPaolo, et al. "Studies on the Carcinolytic Activity of Fumagillin and Some of its Derivatives", Antibiot Annu. 1958-1959;6:541-6.
Drevs, et al. "Antiangiogenic Potency of FK866/K22.175, a New Inhibitor of Intracellular NAD Biosynthesis, in Murine Renal Cell Carcinoma", Anticancer Res. Nov.-Dec. 2003; 23(60):4853-8.
Dumas, et al., "Synthesis and Structure Activity Relationships of Novel Small Molecule Cathepsin D Inhibitors", Bioorg Med Chem Lett. Sep. 6, 1999; 9(17):2531-6.

METHODS OF TREATING A SUBJECT WITH BENIGN PROSTATE HYPERPLASIA

REFERENCE TO RELATED APPLICATIONS

This application is a national stage filing under 35 U.S.C. 371 of PCT/US2011/020515, filed Jan. 7, 2011, which claims priority to U.S. Ser. No. 61/293,320 filed Jan. 8, 2010, all of which are incorporated by reference in their entirety.

BACKGROUND

Benign Prostate Hyperplasia (BPH), also called prostate enlargement, occurs in almost all men as they age. About half of men in their 60s have at least some symptoms of BPH. The prostate is the semen-producing gland that surrounds the urethra, the tube that carries urine from the bladder out of the body. Symptoms of BPH result when the prostate gland grows to the extent that it blocks the flow of urine through the urethra. This blockage may cause urinary problems, including an inability to completely empty the bladder, a frequent urge to urinate, a weak urine stream, nocturia, and hematuria. In some cases, these urinary problems lead to more serious complications, including urinary tract infections; bladder damage, stones, or infection; and kidney damage.

Medications used to control prostate growth include alpha blockers and 5-alpha reductase inhibitors. Alpha blockers may act by relaxing the muscles around the bladder neck, which makes urination easier. Alpha blockers approved by the Food and Drug Administration to treat BPH are terazosin (Hytrin®), doxazosin (Cardura®), tamsulosin (Flomax®) and alfuzosin (Uroxatral®). The long-term effects of alpha-blockers are unknown and side effects include interactions with drugs taken to treat impotence and dizziness and light-headedness upon standing. 5-alpha reductase inhibitors, such as finasteride (Proscar®) and dutasteride (Avodart®) act by shrinking the prostate. 5-alpha reductase drugs may only be effective in subjects with large prostates and not in subjects with moderately-enlarged or normal-sized prostates. In addition, 5-alpha reductase drugs may take up to a year to produce therapeutic effects, may decrease libido, and may interfere with accurate reading of PSA tests, which are used to diagnose prostate cancer.

Non-invasive procedures used to treat BPH include transurethral microwave therapy (TUMT), transurethral needle ablation (TUNA), interstitial laser therapy (ILT), and prostatic stents. TUMT, TUNA, and ILT involve the use of heat produced by microwaves, radio waves, and lasers, respectively, to destroy prostate tissue blocking the urethra. TUMT, TUNA, and ILT may be less effective for large prostates, and the long-term effectiveness of these procedures is unknown. Prostatic stents are metal coils used to prop open the urethra. Stents are typically used in subjects unwilling or unable to take medications and/or have surgery, and are typically not considered to be a long-term treatment option.

Surgeries to treat BPH include transurethral resection of the prostate (TURP), transurethral incision of the prostate (TUIP), laser surgery, and open prostatectomy. In TURP, a narrow instrument is inserted into the urethra and used to scrape away prostate tissue surrounding the urethra. TUIP is performed similarly to TURP, but only one or two cuts in the prostate are made to relieve the pressure on the urethra. Laser surgery, such as photosensitive vaporization of the prostate (PVP) and holium laser enucleation of the prostate (HoLEP) involve the use of lasers to destroy prostate tissue. In an open prostatectomy, the prostate is accessed through an incision is made in a subject's lower abdomen (rather than through the urethra), and the inner portion of the prostate is removed. A subject who undergoes surgery to treat BPH may require additional surgeries if the prostate grows back. Side effects, such as impotence, incontinence, infection and scarring, may occur.

Medications, non-invasive procedures and surgeries known in the art for treating BPH may not be as effective as desired and often produce side effects. Methods of treating subjects with BPH that are more effective than current therapies, e.g., surgery, are clearly needed.

SUMMARY

At least in part, this disclosure provides for a method for treating benign prostatic hypertrophy (BPH) and related disorders, in a male subject in need thereof, comprising administering (e.g. parenterally, intravenously, subcutaneously, orally), a therapeutically effective amount of a MetAP-2. Such methods may result in reduction in the rate of growth of the subject's prostate, for example, such methods may provide for a decrease in the prostate of said male subject by at least 25% within 30 days.

Provided methods may provide that at least one of sperm viability, motility, quantity, and rate of production are not substantially. Contemplated MetAP-2 inhibitors include fumagillin-based compounds.

Provided methods, may, in some embodiments, further comprise administering an additional therapeutic agent, for example, an alpha blocker (e.g. terazosin, doxazosin, tamsulosin and alfuzosin), a 5 alpha reductase inhibitor (e.g. finasteride and dutasteride), saw palmetto, beta-sitosterol, and pygeum. In another embodiment, contemplated methods may further comprise administering a non-invasive procedure, such as transurethral microwave therapy (TUMT), transurethral needle ablation (TUNA), interstitial laser therapy (ILT), orprostatic stents, and/or may further comprise administering a surgical treatment, such as transurethral resection of the prostate (TURP), transurethral incision of the prostate (TUIP), laser surgery, or open prostatectomy.

Exemplary MetAP-2 inhibitors may be, for example, represented by Compound 1:

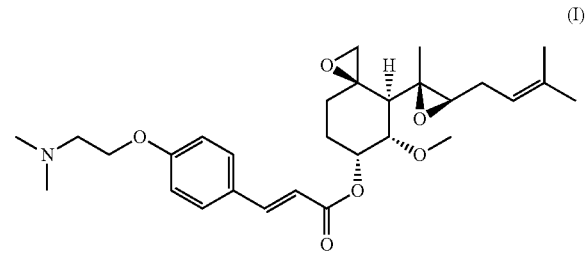 [SMILES: CO[C@@H]1[C@H](OC(=O)/C=C/c2ccc(OCCN(C)C)cc2)CC[C@]2(CO2)[C@H]1[C@@]1(C)O[C@@H]1CC=C(C)C]

(I)

or a pharmaceutically acceptable salt thereof.

MetAP-2 inhibitors may be administered at a dose of about 0.01 mg/kg to about 10 mg/kg, or about 0.04 mg/kg to about 1.0 mg/kg.

Also provided herein is a method for reducing the prostate gland in a male subject in need thereof, comprising administering a therapeutically effective amount of a MetAP-2 inhibitor to the male subject.

DETAILED DESCRIPTION

Overview

The disclosure relates at least in part to methods for treating a prostate condition, such as BPH, which include administering a MetAP2 inhibitor. MetAP2 encodes a protein that functions at least in part by enzymatically removing the amino terminal methionine residue from certain newly translated proteins. Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). While BPH is not a form of cancer, it has been found that MetAP2 inhibitors can effectively treat subjects with BPH. Disclosed herein are methods relating to administering a MetAP-2 inhibitor to treat a prostate condition, e.g., BPH.

BPH may be diagnosed based on an evaluation of a subject's reported symptoms and family history, as well as by the results of one or more tests including a digital rectal exam, urine test, blood test, transrectal ultrasound (TRUS), urodynamic pressure-flow studies, cystoscopy, intravenous pyelogram or CT urogram, prostate-specific antigen (PSA) blood test, urinary flow test, and postvoid residual volume test.

MetAP2 inhibitors

MetAP2 inhibitors refer to a class of molecules that inhibit the activity of MetAP2, e.g., the ability of MetAP2 to cleave the N-terminal methionine residue of newly synthesized proteins to produce the active form of the protein, or the ability of MetAP2 to regulate protein synthesis by protecting the subunit of eukaryotic initiation factor-2 (eIF2) from phosphorylation.

Exemplary MetAP2 inhibitors may include irreversible inhibitors that covalently bind to MetAP2. For example, such irreversible inhibitors include fumagillin, fumagillol, and fumagillin ketone.

Derivatives and analogs of fumagillin, and pharmaceutically acceptable salts thereof are contemplated herein as irreversible MetAP2 inhibitors, such as O-(4-dimethylaminoethoxycinnamoyl)fumagillol (CKD-732, also referred to herein as Compound A), O-(3,4,5-trimethoxycinnamoyl) fumagillol, O-(4-chlorocinnamoyl)fumagillol; O-(4-aminocinnamoyl)fumagillol; O-(4-dimethylaminoethoxycinnamoyl)fumagillol; O-(4-methoxycinnamoyl)fumagillol; O-(4-dimethylaminocinnamoyl)fumagillol; O-(4-hydroxycinnamoyl)fumagillol; O-(3,4-dimethoxycinnamoyl)fumagillol; O-(3,4-methylenedioxycinnamoyl)fumagillol; O-(3,4,5-trimethoxycinnamoyl)fumagillol; O-(4-nitrocinnamoyl) fumagillol; O-(3,4-dimethoxy-6-aminocinnamoyl) fumagillol; O-(4-acetoxy-3,5-dimethoxycinnamoyl) fumagillol; O-(4-ethylaminocinnamoyl)fumagillol; O-ethylaminoethoxycinnamoyl)fumagillol; O-(3-dimethylaminomethyl-4-methoxycinnamoyl)fumagillol; O-(4-trifluoromethylcinnamoyl)fumagillol; O-(3,4-dimethoxy-6-nitrocinnamoyl)fumagillol; O-(4-acetoxycinnamoyl) fumagillol; O-(4-cyanocinnamoyl)fumagillol; 4-(4-methoxycinnamoyl)oxy-2-(1,2-epoxy-1,5-dimethyl-4-hexenyl)-3-methoxy-1-chloromethyl-1-cyclohexanol; O-(3, 4,5-trimethoxycinnamoyl)fumagillol; O-(4-dimethylaminocinnamoyl)fumagillol; O-(3,4,5-trimethoxycinnamoyl)oxy-2-(1,2-epoxy-1,5-dimethyl-4-hexenyl)-3-m-ethoxy-1-chloromethyl-1-cyclohexanol; O-(4-dimethylaminocinnamoyl)oxy-2(1,2-epoxy-1,5-dimethyl-4-hexenyl)-3-me-thoxy-1-chloromethyl-1-cyclohexanol; O-(3,5-dimethoxy-4-hydroxycinnamoyl)fumagillol or O-(chloracetyl-carbamoyl) fumagillol (TNP-470).

Fumagillin, and some derivatives thereof, have a carboxylic acid moiety and can be administered in the form of the free acid. Alternatively, contemplated herein are pharmaceutically acceptable salts of fumagillin, fumagillol, and derivatives thereof. Pharmaceutically acceptable salts illustratively include those that can be made using the following bases: ammonia, L-arginine, benethamine, benzathene, betaine, bismuth, calcium hydroxide, choline, deanol, diethanolamine, diethylamine, 2-(diethylamino)ethanol, ethylenediamine, N-methylglucamine, hydrabamine, 1H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, diclyclohexlamine, or any other electron pair donor (as described in Handbook of Pharmaceutical Salts, Stan & Wermuth, VHCA and Wiley, Uchsenfurt-Hohestadt Germany, 2002). Contemplated pharmaceutically acceptable salts may include hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Esters of the present invention may be prepared by reacting fumagillin or fumagillol with the appropriate acid under standard esterification conditions described in the literature (Houben-Weyl 4th Ed. 1952, Methods of Organic, Synthesis). Suitable fumagillin esters include ethyl methanoate, ethyl ethanoate, ethyl propanoate, propyl methanoate, propyl ethanoate, and methyl butanoate.

In another embodiment, contemplated irreversible inhibitors of MetAP2 may include a siRNA, shRNA, an antibody or an antisense compound of MetAP2.

Further examples of MetAP2 inhibitors, are provided in the following references, each of which is hereby incorporated by reference: Olson et al. (U.S. Pat. No. 7,084,108 and WO 2002/042295), Olson et al. (U.S. Pat. No. 6,548,477; U.S. Pat. No. 7,037,890; U.S. Pat. No. 7,084,108; U.S. Pat. No. 7,268, 111; and WO 2002/042295), Olson et al. (WO 2005/066197), Hong et al. (U.S. Pat. No. 6,040,337), Hong et al. (U.S. Pat. No. 6,063,812 and WO 1999/059986), Lee et al. (WO 2006/080591), Kishimoto et al. (U.S. Pat. No. 5,166,172; U.S. Pat. No. 5,698,586; U.S. Pat. Nos. 5,164,410; and 5,180,738), Kishimoto et al. (U.S. Pat. No. 5,180,735), Kishimoto et al. (U.S. Pat. No. 5,288,722), Kishimoto et al, (U.S. Pat. No. 5,204,345), Kishimoto et al. (U.S. Pat. No. 5,422,363), Liu et al. (U.S. Pat. No. 6,207,704; U.S. Pat. No. 6,566,541; and WO 1998/056372), Craig et al. (WO 1999/057097), Craig et al. (U.S. Pat. No. 6,242,494), BaMaung et al. (U.S. Pat. No. 7,030,262), Comess et al. (WO 2004/033419), Comess et al. (U.S. Pat. No. 2004/0157836), Comess et al. (U.S. Pat. No. 2004/0167128), Henkin et al. (WO 2002/083065), Craig et al. (U.S. Pat. No. 6,887,863), Craig et al. (U.S. 2002/0002152), Sheppard et al. (2004, Bioorganic & Medicinal Chemistry Letters 14:865-868), Wang et al. (2003, Cancer Research 63:7861-7869), Wang et al. (2007, Bioorganic & Medicinal Chemistry Letters 17:2817-2822), Kawai et al. (2006, Bioorganic & Medicinal Chemistry Letters 16:3574-3577), Henkin et al. (WO 2002/026782), Nan et al. (US 2005/01 13420), Luo et al. (2003, J. Med. Chem., 46:2632-2640), Vedantham et al. (2008, J. Comb. Chem., 10:195-203), Wang et al. (2008, J. Med. Chem 51:6110-20), Ma et al. (2007, BMC Structural Biology, 7:84) and Huang et al. (2007, J. Med. Chem., 50:5735-5742), Evdokimov et al. (2007, PROTEINS: Structure, Function, and Bioinformatics, 66:538-546), Garrabrant et al. (2004, Angiogenesis 7:91-96), Kim et al. (2004, Cancer Research, 64:2984-2987), Towbin et al. (2003, The Journal of Biological Chemistry, 278(52):52964-52971), Marino Jr. (U.S. Pat. No. 7,304,082), Kallender et al. (U.S. patent application number 2004/0192914), and Kallender et al. (U.S. patent application numbers 2003/0220371 and 2005/0004116). In some embodiments, contemplated MetAP2 inhibitors do not include fumagillin, fumagillol, fumagillin ketone, CKD-732/Compound A, and/or TNP-470.

For example, contemplated MetAP2 inhibitors may include:

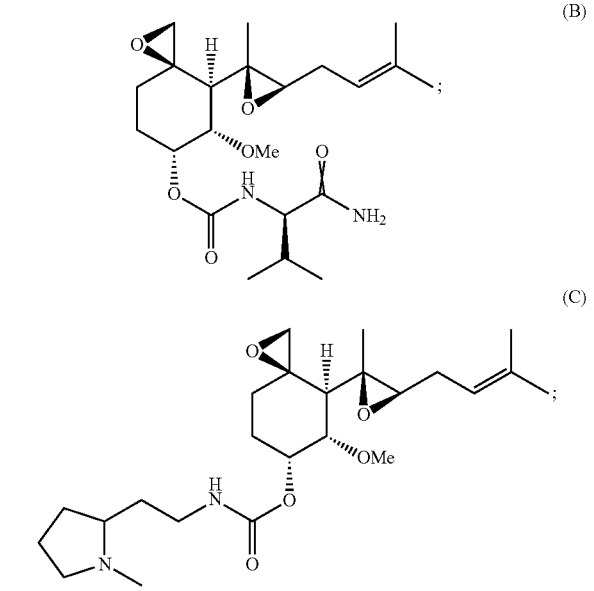

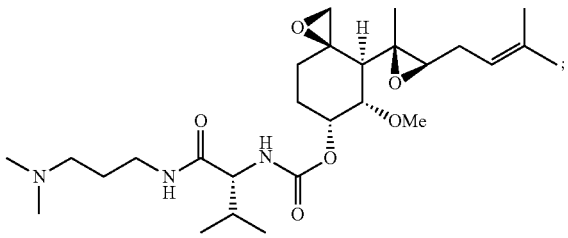

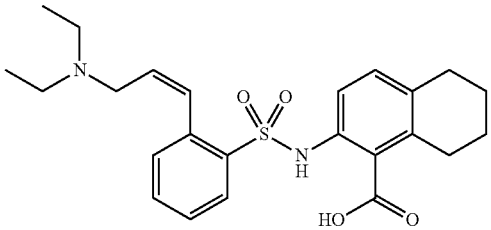

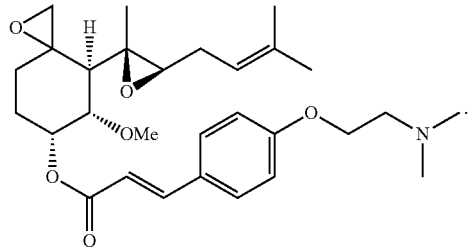

Methods

A method of treating a condition affecting the prostate, e.g., benign prostate hyperplasia (BPH), in a subject in need thereof is provided herein, comprising parenterally or non-parenterally administering a therapeutically effective amount of a MetAP2 inhibitor to said subject. In some embodiments, a contemplated therapeutically effective amount of a MetAP2 as described below, does not substantially modulate or suppress angiogenesis, but is still effective as MetAP2 inhibitor. The term "angiogenesis" is known to persons skilled in the art, and refers to the process of new blood vessel formation, and is essential for the exponential growth of solid tumors and tumor metastasis. For example, provided herein is a method of treating a condition affecting the prostate in a subject in need thereof, comprising administering a therapeutically effective amount of a MetAP2 inhibitor to said subject, wherein substantially no loss of new blood vessels in the prostate or other tissue compartments occur as compared to a subject being treated for a prostate condition with, e.g., surgery.

In some embodiments, disclosed methods, upon administration of said MetAP2 inhibitor e.g. daily or weekly, for about 3, 4, 5 or 6 months or more may result in a reduction in the rate of prostate growth in a male subject of at least a 5%, 10%, 20%, or 30%, or more based on the prostate's original rate of growth. In some embodiments, disclosed methods, upon administration of said MetAP2 inhibitor e.g. daily or weekly, for about 3, 4, 5 or 6 months or more may result in a reduction in the size of a prostate of at least a 5%, 10%, 20%, or 30%, or more based on the original size of the prostate. In an embodiment, reduction in size of the prostate following treatment with therapeutically effective doses of MetAP2 inhibitors may substantially cease once a subject attains a desired prostate size, i.e., a size that reduces and/or eliminates symptoms, e.g. urinary symptoms, of a prostate condition, e.g. BPH.

Some methods disclosed herein may involve co-administration of another BPH treatment, such as a therapeutic agent. Therapeutic agents include but are not limited to alpha blockers, e.g., terazosin (Hytrin®), doxazosin (Cardura®), tamsulosin (Flomax®) and alfuzosin (Uroxatral®), 5-alpha reductase inhibitors, e.g., finasteride (Proscar®) and dutasteride (Avodart®), saw palmetto, beta-sitosterol, and pygeum. In some embodiments, contemplated methods include co-administration of a non-invasive procedure, e.g., transurethral microwave therapy (TUMT), transurethral needle ablation (TUNA), interstitial laser therapy (ILT), and prostatic stents. Further embodiments include co-administering a surgical treatment, e.g. transurethral resection of the prostate (TURP), transurethral incision of the prostate (TUIP), laser surgery, and open prostatectomy.

In some embodiments, co-administration of a MetAP-2 inhibitor and another BPH treatment occur at the same time. In other embodiments, administration of a MetAP-2 inhibitor occurs immediately prior to or immediately after another BPH treatment. In yet another embodiment, a period of time may elapse between administration of a MetAP-2 inhibitor and another BPH treatment. For example, a male subject may be administered prostate surgery to reduce the size of the prostate, followed by a recovery period of, e.g., 1 week, 2 weeks, 3 weeks, 4 weeks, 2 months, or 6 months or longer, after which time the male subject is administered a MetAP-2 inhibitor to reduce the rate of re-growth of the prostate.

Administration and Formulation

Contemplated herein are formulations suitable for parenteral or non-parenteral administration of MetAP2 inhibitors. In certain embodiments, a subject may have a lower systemic exposure (e.g. at least about 2, 3, 5, 10, 20, or at least about 30% less systemic exposure) to the non-parenterally (e.g. orally) administered of a MetAP2 inhibitor as compared to a subject parenterally (e.g. subcutaneously) administered the same dose of the MetAP2 inhibitor. For example, non-parenterally (e.g. orally) administered MetAP2 inhibitors may bind less to MetAP2 as compared to parenterally (e.g. subcutaneously) administered MetAP2 inhibitors.

Contemplated non-parenteral administration includes oral, buccal, transdermal (e.g. by a dermal patch), topical, inhalation, sublingual, ocular, pulmonary, nasal, or rectal administration.

Contemplated parenteral administration includes intravenous and subcutaneous administration, as well as administration at a site of a minimally-invasive procedure or a surgery.

In another embodiment, provided herein are effective dosages, e.g. a daily dosage of a MetAP2 inhibitor, that may not substantially modulate or suppress angiogenesis. For example, provided here are methods that include administering doses of MetAP2 inhibitors that are effective for reducing the rate of growth of the prostate, but are significantly smaller doses than that necessary to modulate and/or suppress angiogenesis (which may typically require about 12.5 mg/kg to about 50 mg/kg or more). For example, contemplated dosage of a MetAP2 inhibitor in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day.

For example, an effective amount of the drug for reducing the rate of prostate growth in a male subject may be about 0.0001 mg/kg to about 25 mg/kg of body weight per day. For example, a contemplated dosage may from about 0.001 to 10 mg/kg of body weight per day, about 0.001 mg/kg to 1 mg/kg of body weight per day, about 0.001 mg/kg to 0.1 mg/kg of body weight per day or about 0.005 to about 0.04 mg/kg or about 0.005 to about 0.049 mg/kg of body weight a day. In an embodiment a MetAP2 inhibitor such as disclosed herein (e.g. O-(4-dimethlyaminoethoxycinnamoyl)fumagillol); may be administered about 0.005 to about 1 mg/kg, or to about 5 mg/kg, or about 0.005 to about 0.1 mg/kg of a subject.

For example, provided herein is a method for treating a prostate condition in a male subject in need thereof, comprising administering, parenterally (e.g. intravenously) or non-parenterally, about 0.005 to about 0.04 mg/kg of a MetAP2 inhibitor selected from O-dimethylaminoethoxycinnamoyl) fumagillol and pharmaceutically acceptable salts thereof (for example, an oxalate salt), to said subject. Such a method, upon administration of said MetAP2 inhibitor e.g. daily or weekly, for about 3, 4, 5 or 6 months or more may result in at least a 10%, 20%, 30%, or 40% or more reduction in the rate of growth of the prostate.

Contemplated methods may include administration of a composition comprising a MetAP2 inhibitor, for example, hourly, twice hourly, every three to four hours, daily, twice daily, 1, 2, 3 or 4 times a week, every three to four days, every week, or once every two weeks depending on half-life and clearance rate of the particular composition or inhibitor.

Treatment can be continued for as long or as short a period as desired. The compositions may be administered on a regimen of, for example, one to four or more times per day. A suitable treatment period may be, for example, at least about one week, at least about two weeks, at least about one month, at least about six months, at least about 1 year, or indefinitely. A treatment period may terminate when a desired result, for example desired prostate size, is achieved. For example, treatment may terminate when reduction of about 20% of the prostate, about 30% of the prostate or more has been achieved. A treatment regimen may include a corrective phase, during which a MetAP2 inhibitor dose sufficient to provide reduction of prostate size is administered, followed by a maintenance phase, during which a lower MetAP2 inhibitor dose sufficient to reduce or prevent growth is administered.

For pulmonary (e.g., intrabronchial) administration, MetAP2 inhibitors may be formulated with conventional excipients to prepare an inhalable composition in the form of a fine powder or atomizable liquid. For ocular administration, MetAP2 inhibitors may be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups And elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

When administered in lower doses, injectable preparations are also contemplated herein, for example, sterile injectable aqueous or oleaginous suspensions may be formulated according to the known art using suitable dispersing or wetting agents and suspending agents.

Compositions for rectal administration may be suppositories which can be prepared by mixing a MetAP2 inhibitor with suitable non-irritating excipients or carriers such as cocoa butter, polyethylene glycol or a suppository wax which are solid at ambient temperature but liquid at body temperature and therefore melt in the rectum and release the active agent(s). Alternatively, contemplated formulations can be administered by release from a lumen of an endoscope after the endoscope has been inserted into a rectum of a subject.

Oral dosage forms, such as capsules, tablets, pills, powders, and granules, may be prepared using any suitable process known to the art. For example, a MetAP2 inhibitor may be mixed with enteric materials and compressed into tablets.

Alternatively, formulations of the invention are incorporated into chewable tablets, crushable tablets, tablets that dissolve rapidly within the mouth, or mouth wash.

EXAMPLE

This example is not intended in any way to limit the scope of this invention but is provided to illustrate aspects of the disclosed methods. Many other embodiments of this invention will be apparent to one skilled in the art.

Example 1

Administration of a MetAP-2 Inhibitor to Reduce Prostate Size

Male rats were divided into a control group and three test groups with 20 animals per group. Animals were administered the MetAP-2 inhibitor Compound I, represented by the formula:

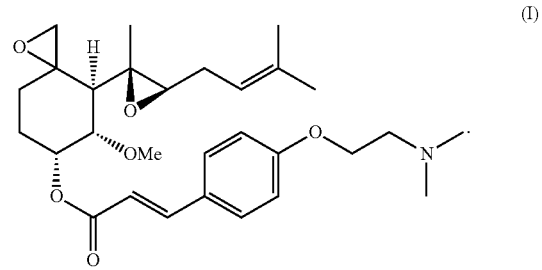 [SMILES: CO[C@@H]1[C@H](OC(=O)/C=C/c2ccc(OCCN(C)C)cc2)CCC2(CO2)[C@H]1[C@@]1(C)O[C@@H]1CC=C(C)C]

(I)

Compound I was prepared in a 5% mannitol solution was administered once daily for four weeks by a fifteen-minute intravenous infusion according to Table I.

TABLE I

| Group Number | Test Article | Dosage Level (mg/kg/day) | Dosage Concentration (mg/mL) | Dosage Volume (mL/kg) | Infusion Rate (mL/kg/min) | Number of Males |
|---|---|---|---|---|---|---|
| 1 | Vehicle Control | 0 | 0 | 3.75 | 0.25 | 20 |
| 2 | Compound I | 0.04 | 0.01 | 3.75 | 0.25 | 20 |
| 3 | Compound I | 0.2 | 0.053 | 3.75 | 0.25 | 20 |
| 4 | Compound I | 1.0 | 0.266 | 3.75 | 0.25 | 20 |

Ten animals from each group were euthanized at the end of the four weeks.

The remaining ten animals were allowed to recover for 10 additional weeks and were then euthanized. Body weights and organ weights (absolute and relative to body weights) were determined and are shown in Table II.

TABLE II

| | Group | | | |
|---|---|---|---|---|
| | 0 mg/kg/day (Vehicle Control) | 0.04 mg/kg/day | 0.2 mg/kg/day | 1.0 mg/kg/day |
| Final Body Weight (g) | | | | |
| Mean | 477 | 437** | 411** | 393** |
| Standard Deviation | 37.8 | 28.9 | 19.4 | 17.9 |
| N | 10 | 10 | 10 | 10 |
| Prostate Weight (g) | | | | |
| Mean | 1.23 | 0.90** | 0.89** | 0.76** |
| Standard Deviation | 0.255 | 0.188 | 0.166 | 0.190 |
| N | 10 | 10 | 10 | 10 |

**Significantly different from the control group at 0.01 using Dunnett's test

Administration of a MetAP-2 inhibitor at all doses causes a reduction in the weight of the prostate gland in male animals.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and

What is claimed is:

1. A method for treating benign prostatic hypertrophy (BPH) in a male subject in need thereof, comprising administering a therapeutically effective amount of a MetAP-2 inhibitor to said male subject.

2. The method of claim 1, wherein the MetAP-2 inhibitor is a fumagillin-based compound.

3. The method of claim 1, wherein the method results in a reduction in the rate of growth of the subject's prostate.

4. The method of claim 1, wherein upon administration, the prostate of said male subject decreases by at least 25% within 30 days.

5. The method of claim 1, wherein administration occurs parenterally.

6. The method of claim 1, wherein administration is intravenous or subcutaneous.

7. The method of claim 1, wherein at least one of sperm viability, motility, quantity, and rate of production are not substantially decreased after administration of said MetAP-2 inhibitor.

8. The method of claim 1, further comprising administering an additional therapeutic agent.

9. The method of claim 8, wherein the additional therapeutic agent is selected from the group consisting of an alpha blocker, a 5 alpha reductase inhibitor, saw palmetto, beta-sitosterol, and pygeum.

10. The method of claim 9, wherein the alpha blocker is selected from the group consisting of terazosin, doxazosin, tamsulosin and alfuzosin.

11. The method of claim 9, wherein the 5 alpha reductase inhibitor is selected from the group consisting of finasteride and dutasteride.

12. The method of claim 1, further comprising administering a non-invasive procedure.

13. The method of claim 12, wherein the non-invasive procedure is selected from the group consisting of transurethral microwave therapy (TUMT), transurethral needle ablation (TUNA), interstitial laser therapy (ILT), and prostatic stents.

14. The method of claim 1, further comprising administering a surgical treatment.

15. The method of claim 14, wherein the surgical treatment is selected from the group consisting of transurethral resection of the prostate (TURP), transurethral incision of the prostate (TUIP), laser surgery, and open prostatectomy.

16. A method for treating benign prostatic hypertrophy (BPH) in a male subject in need thereof, comprising administering a therapeutically effective amount of Compound I, represented by:

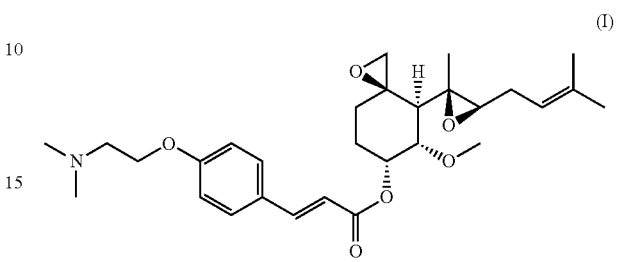

or a pharmaceutically acceptable salt thereof to said male subject.

17. The method of claim 1, wherein the MetAP-2 inhibitor is administered at a dose of about 0.01 mg/kg to about 10 mg/kg.

18. The method of claim 1, wherein the MetAP-2 inhibitor is administered at a dose of about 0.04 mg/kg to about 1.0 mg/kg.

19. A method for reducing the prostate gland in a male subject in need thereof, comprising administering a therapeutically effective amount of a MetAP-2 inhibitor to a male subject in need thereof.

20. A method for reducing the prostate gland in a male subject in need thereof, comprising administering a therapeutically effective amount of a Compound I, represented by:

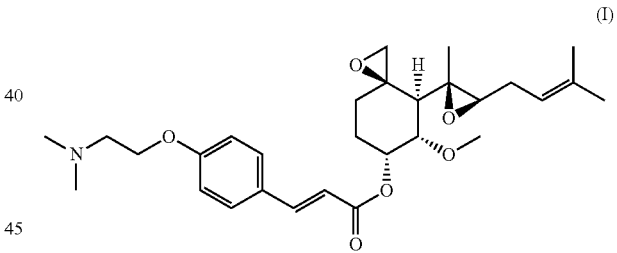

or a pharmaceutically acceptable salt thereof to a male subject in need thereof.

* * * * *